United States Patent
Sasaki et al.

(10) Patent No.: US 6,277,419 B1
(45) Date of Patent: Aug. 21, 2001

(54) METHODS OF ENHANCING VITALITY OF PLANTS TREES AND CROPS WITH STEVIA

(75) Inventors: Yoshinori Sasaki, Ohita-ken; Masafumi Tanaka, Kumamoto-ken; Naohiko Sato, 32-14, Chofugaoka 2-Chome, Chofu-shi, Tokyo-to, all of (JP)

(73) Assignee: Naohiko Sato, Tokyo-to (JP)

( * ) Notice: Subject to any disclaimer, the term of this patent is extended or adjusted under 35 U.S.C. 154(b) by 0 days.

(21) Appl. No.: 09/506,516

(22) Filed: Feb. 17, 2000

(51) Int. Cl.⁷ ............................ A61K 35/78; C12N 5/00; C12N 5/02
(52) U.S. Cl. ................... 424/774; 424/779; 435/420; 435/431
(58) Field of Search ............................... 424/195.1, 774, 424/779; 435/420, 431

(56) References Cited

U.S. PATENT DOCUMENTS

| 5,250,300 | 10/1993 | Dozono | 424/195.1 |
| 5,250,301 | 10/1993 | Dozono | 424/195.1 |
| 5,262,161 | 11/1993 | Dozono | 424/195.1 |

FOREIGN PATENT DOCUMENTS

| 0880894 | 12/1998 | (EP) . |
| 57206603 | * 12/1982 | (JP) . |
| 62-108790 | 5/1987 | (JP) . |
| 62-108791 | 5/1987 | (JP) . |
| 62108790 | 5/1987 | (JP) . |
| 62108791 | 5/1987 | (JP) . |
| 03220109 | * 1/1990 | (JP) . |
| 3-31207 | 2/1991 | (JP) . |
| 03177386 | * 8/1991 | (JP) . |
| 3-177386 | 8/1991 | (JP) . |
| 3-220109 | 9/1991 | (JP) . |

* cited by examiner

Primary Examiner—Christopher R. Tate
(74) Attorney, Agent, or Firm—Jordan and Hamburg LLP

(57) ABSTRACT

Stevia particles of at least 10 $\mu$m diameter and/or liquid extract is applied to soil in which plants are cultivated and/or to the plants. The Stevia is applied in a quantity per unit area effective for at least one of the following effects: enhancing root growth of plants, prolonging freshness and tastiness of edible agricultural products yielded by the plants, decreasing the dropping of fruit before harvest time, aiding the sustaining and multiplying of microbes in the soil beneficial to the plants, countering soil damage which would otherwise occur due to repeated plantings, moderating the absorption of fertilizer by the plants in the event of excessive application of fertilizers, and making the plants more resistant to harmful microbes in the soil.

18 Claims, No Drawings

METHODS OF ENHANCING VITALITY OF PLANTS TREES AND CROPS WITH STEVIA

BACKGROUND OF THE INVENTION

The present invention relates generally to enhancing growth of plants, trees, and/or crops. More specifically, the invention relates to methods of enhancing growth of plants, trees, and crops with Stevia.

It is generally known that Stevia contains such very strong sweet substances such as Stevioside and Rebaudioside. In JP62-108790 and 62-108791, the mixture of the pulverized leaves and stalk of the Stevia plant, where the pulverized leaves portion shall be between 10% and 40% by weight and it is strictly required that the particles be no greater than 0.3 $\mu$m in diameter, is disclosed for use in the cultivation of plants. When applied as an additive to the fertilizers, the mixture acts to bring out the natural taste and sweetness, and also improves the taste, flavor, luster, corpulence, and size of fruits and other agricultural products.

SUMMARY OF THE INVENTION

The invention hereunder relates to use of the plant tissues of the leaves and stalk of Stevia, which enhance the vital and resistant powers of plants, trees, and crops, and which accelerate the growth of the roots of plants, trees, and crops. It is understood that the term "plants" as used herein, when not referring to a specific plant, is intended to encompass all plantlike, including trees. It has been determined according to the invention that use of Stevia in the form of particles of diameter at least 10 $\mu$m or in the form of a liquid extract of Stevia results in effects neither disclosed by nor obvious from the prior art, which, moreover, does not disclose or make obvious any agricultural use of a liquid extract of Stevia. In further accordance with the invention, particular modes of application of pulverized Stevia of particular diameters much greater than in the prior art and of liquid extracts of Stevia and particular effects resulting from applying these to plants and/or to the soil in which the plants are planted have been determined. The Stevia powder or liquid extract may be applied to the plants and/or to the soil in which the plants are planted. Practically speaking, it is convenient to refer to application of the Stevia powder or extract to the soil. On this basis, for example, applications per unit area are determined. It is to be understood, however, that recitations of application of Stevia particles or liquid extract to the soil are not intended to exclude application of the Stevia particles and/or liquid extract to the plants as well because, of course, the plants are not shielded during application of the Stevia particles or liquid extract.

The mixture of the dry and pulverized plant tissues of the leaves and stalk of Stevia has, according to the invention, been found to have the following effects when applied to the soil:

(1) It makes the taste of the crops last longer;
(2) Even when fertilizer is excessively applied, the plants, trees, and crops absorb only the required quantity of the mixture and grow without any problem;
(3) It makes the plants, trees, and crops more resistant to harmful microbes contained in the soil;
(4) It accelerates the growth of roots;
(5) It proliferates useful microbes contained in the soil;
(6) It prevents problems generally associated with repeated cultivation;
(7) It prevents fruits from falling off the trees before the harvest.

It has been determined, according to the invention, that hot water extract of the finely pulverized powder of the plant tissue of Stevia acts to vitalize plants, trees, and crops when applied even in small quantity to the plants and/or the soil in which the plants are planted and has the same effects as the pulverized Stevia according to the invention.

Even though the materials of the invention act to vitalize plants, trees, and crops when they are administered only once to the soil in a small quantity, the materials are more effective when administered two or more times at regular intervals. Compost is a desirable fertilizer and acts to vitalize the land laid to waste by the excessive application of chemical fertilizers. However, the application of 1–20 gram per square meter of compost is not effective at all. The substances of the invention have conspicuous effects even in small quantity; thus, they are not fertilizers but vitality-enhancing materials.

DETAILED DESCRIPTION OF THE INVENTION

The raw material of the invention, which is referred to herein simply as Stevia, is a perennial composite plant, academically called *Stevia Rebaudiana Bertoni*, with its related plants originally growing in South America. The effective substances are contained in the whole mature body of the plant, especially in the leaves and stalk of the plant before budding occurs. They are also contained in the root and seedling of the plant in one-fifth to one-tenth of that contained in the stalk.

To produce the finely pulverized powder of Stevia, the part of Stevia above the soil is cut off and removed from the soil, dried, and pulverized. There is no specific way of drying and pulverizing it. It only should not be dried under rainy or dewy conditions. After separating the leaves and the stalk from one another and cutting the stalk into smaller pieces, the separated portions are separately pulverized. Pulverization after drying is the most effective way of producing the fine powder. The moisture contained within the mixture is preferably less than about, by weight, 12% and more preferably less than about, by weight, 10.5%. The diameter of the particles of the powder is at least 10 $\mu$m and preferably less than about 100 $\mu$m and more preferably less than about 50 $\mu$m.

It has been found that the effectiveness of Stevia powder or Stevia extract according to the invention is increased by the addition thereto of an organic acid. Preferred for this purpose are acetic acid, lactic acid, propionic acid, citric acid, tartaric acid, malic acid, valeric acid and maleic acid.

The effective substances of the invention hereunder have not yet been identified. However, it is recognized that hot water extracts of the finely pulverized powder have a very strong antioxidant activity.

The quantity to be applied of material according the invention varies with the kind of agricultural products and with the condition of the soil. But generally, about 1–20 grams per square meter, preferably about 2–15 grams per square meter and more preferably about 5–10 grams per square meter are applied at a time. In some instances, an application as light as about 0.2 gram per square meter or as heavy as about 100 grams per square meter or greater may be used. A single application is sufficient to produce the vitalization effects. To make sure the plants, trees and crops receive the effects, multiple spraying may be done before harvest. In cases where plants, trees and crops are young and fragile with the soil being full of harmful microbes or with the soil being damaged by repeated crops, about 12–15 grams per square meter may be sprayed. As will be explained hereinafter, materials according to the invention may be applied in quantities per unit area different from those mentioned hereinabove for particular crops and purposes.

Maintaining the hot water extract of the plant tissue of Stevia at room temperature, the extract ferments and emits carbon dioxide. It ferments vigorously at the initial stage and slowly after 3–6 months. It still ferments, though slightly, even after 1 to 5 years. The fermented liquid has the same effects as the pulverized powder of Stevia, such as lengthening the period harvested fruits, vegetables and the like stay fresh, preventing fruits from falling down off the trees, keeping the microbes contained in the soil, preventing damage caused by repeated plantings and harvests, and accelerating the expansion of the roots. The fermented liquid extract will usually be sold in a concentration of about 13–18% by weight solids content. When actually used, that product is to be diluted up to about 300 to 3000 times, by volume, with water and then applied to plants and/or the soil in which they are growing. The amount to be applied may be calculated as volume of the liquid per unit area of the soil to which the liquid is applied, for example, liters per square meter. The calculation may be made, for example, to apply the same amount of solids per unit area as would be applied in the case of pulverized Stevia which has not been made into a liquid extract.

While plants have a self-protection mechanism whereby they do not absorb more nutrients than needed, when plants are deficient in physical strength, their growth is obstructed because they excessively absorb nitrogen, especially nitrate nutrients. With the pulverized powder or liquid extract of Stevia added to the fertilizers, the plants can enhance their physical strength and grow more stably without the excessive absorption of nutrients in the soil.

Fruit trees that develop so as to bear many fruits, especially citrus fruit trees, get exhausted and cannot expand their roots. The expansion of the roots is proportional to quantity of fruit in future harvests. With the roots expanded, also the taste of the fruit is improved Trees bearing dekopon, a kind of mandarin orange, are poor in root expansion and the harvest therefrom decreases harvest by harvest even if it comes to the point that they bear fruit only every other year. Prior to this invention, there has been no effective way of expanding the roots. The inventors hereunder detected that the Stevia powder or liquid extract expands the roots by application of the powder or liquid extract to the soil. The amount of Stevia to be applied is preferably about 2–15 kg per 1000 square meters.

The pulverized powder or liquid extract of the plant tissue of Stevia acts to accelerate the rooting of various plants, including fruit trees. Being applied in small quantity, the effective materials contained in the powder are considered to have some vitality enhancing activity for plants and not to act as a fertilizer.

EXAMPLE 1

Preparation of a Powder from Stevia Plant

A Stevia plant, before budding, is cut off and removed from the surface of the soil. The leaves and stalk are separated after being dried naturally. After the stalk is cut into pieces and dried naturally, the leaves and the stalk pieces are separately pulverized by a pulverizing machine with rotating cutters. Since the leaves and the stalk pieces cannot be pulverized into particles of the desired size by the pulverizing machine, both portions separately undergo a two-step pulverizing process so that particles of 20–30 $\mu$m are obtained. The pulverized powders of the stalk and of the leaves are mixed in a ratio of stalk to leaves of about 8:2 by weight. It is this Stevia powder which is used in the subsequent examples wherever application of Stevia powder is mentioned.

Part of the mixture is boiled for 3–8 hours. The hot water extract is condensed to a solids concentration of 16% by weight and placed at room temperature. The extract ferments vigorously initially and emits carbon dioxide. After 5–6 months, the carbon dioxide generated decreases. The fermented extract remaining after one year is the Stevia liquid extract.

EXAMPLE 2

Experiment Regarding the Period of Time Harvested Spinach Remains Fresh

Spinach seeds are planted in experimental areas A and B (9 square meters each) on September 14. Spinach is harvested on October 15. The same fertilizer is administered to both A and B. Pulverized powder of Stevia is applied to the surface of the soil of area A at a ratio of 5 g per square meter followed by sprinkling the surface of the soil with water on October 1 and 7. Stevia powder is not applied to Area B.

The spinach harvested from areas A and B have dark green and lively colors and look identical at first sight. The spinach harvested from areas A and B are separately wrapped in newspapers and stored at a temperature of 20° C. After 7 days, the spinach from area A is as fresh and as lively in appearance as when first observed, but loses some of its freshness on the 8th day. The spinach from area B stays fresh only for 2 days and loses it on the 3rd day; on the 4th day, there are some withered and brown leaves.

EXAMPLE 3

Experiment Regarding the Period of Time Harvested Peaches Remain Fresh

A peach orchard (200 square meters) having 14 peach trees is divided into 2 blocks of equal area having 7 peach trees, making one block the experimental area A and the other area B. The same fertilizer is applied to both areas A and B as usual (namely, a mixed fertilizer is administered at a ratio of 10 kg per square meter four times every other month).

10 days before budding occurs on the peach trees, pulverized powder of Stevia is applied over the surface of the soil of area A at a ratio of 10 g per square meter, and then Area A is sprinkled with water. And at the time when the leaves of the peach trees become 3 cm long, the fermented liquid of Stevia described in Example 1 is sprayed on the surface of the soil of Area A at a ratio of a predetermined amount of ml per square meter to result in an application on a solids basis of 10 g per square meter. Neither powder nor liquid of Stevia is applied to area B.

The peaches harvested from area A are all ripened and stay fresh for 12–15 days after being harvested, while only some of the peaches harvested from area B are ripened and stay fresh only 2–3 days after being harvested. The unripened peaches from area B are delivered to the market and stay fresh about 2 weeks. Additionally, the peaches from area B turns brown later when pressed by fingers, but those from area A do not turn brown later even when pressed by fingers.

EXAMPLE 4

Experiment Regarding the Period of Time Harvested Mandarin Oranges Remain Fresh A mandarin orange orchard (2000 square meters) having 150 mandarin orange trees is divided into 2 blocks of equal area and equal number of trees, one being experimental area A and the other area B. The same fertilizer is administered to both areas A and B (namely, a mixed fertilizer is sprayed at a ratio of 10 kg per 100 square meters four times every other month). Stevia powder is sprayed over the surface of the soil of area A at a ratio of 7 g per square meter on October 6 and 10. No powder is sprayed over area B. The crop from each of areas A and B is 3.5 tons.

The crops from areas A and B are placed in respective sets of corrugated cardboard boxes at room temperature in December. A white color mold forms on the crop from area B in February and the crop becomes totally rotten in a white color in early March. The crop from area A does not get moldy even in April, and has a little loss of moisture.

EXAMPLE 5

Experiment Regarding Preventing Peaches from Falling off the Trees

A peach orchard in which white peaches are cultivated is divided into 2 equal blocks each of 50 square meters, one being experimental area A and the other area B. Before budding takes place on the trees, pulverized powder of Stevia is sprayed in a circle on the soil around each tree in area A at a ratio of 5 g per square meter, totaling 250 g of the powder for area A of the orchard, and then area A is spriked with water. This spraying is repeated when the flowers from the trees start falling down, when the trees begin bearing fruit, and when the fruit becomes 3 cm long. The manner of cultivation of area A is the same as that of area B, except for the spraying of the Stevia powder. The proportion of fruits that fall down is 5.1% in area A and is 17% in area B.

The natural falling down of fruits from fruit trees is caused by the self-protection mechanism of the fruit trees. The applied powder of the plant tissue of Stevia acts to increase the vitality of the trees. The effect of preventing the falling down of fruits from fruit trees is conspicuous for pear trees, apple trees, and peach trees.

EXAMPLE 6

Experiment Regarding Maintaining or Acquiring a Normal Level of Microbes Living in Soil Seedlings of Japanese black pine are planted on April 5, the seedlings having a height of 40 cm and a diameter at the root of 1 cm. One experimental area is 3.5 meters long and 1 meter wide, being 3.5 square meters, and has about 30 seedlings planted there. There are two other similar experimental areas, with the number of seedlings totaling 85. There are three corresponding control areas having 87 seedlings.

5000 microbes belonging to the group of Shimabara are inoculated per seedling on August 30. 300 g of pulverized Stevia powder is sprayed over the surface of the experimental area, and 5 liters of water per area are sprayed over each area after the inoculation. The height and diameter (the latter at 5 cm above the surface of the soil) of each seedling is measured on June 13 (designated as the start in subsequent tables) and again on November 7 (designated as the finish in subsequent tables).

In the investigation at the time of the finish, the seedlings are divided into three groups, the healthy ones having green leaves, the semi-withered ones with one-third to one-half of the leaves being yellowish brown, and the withered ones with all leaves being brown. The results are shown in Table 1 below consisting of three sub-tables.

TABLE 1

|  | The Invention Hereunder | Control Areas |
| --- | --- | --- |
| Healthy | 23 (27.1%) | 13 (14.9%) |
| Semi-withered | 48 (56.5%) | 54 (62.1%) |
| Withered | 14 (16.5%) | 20 (23.0%) |

| Comparison of the height of seedlings | | | | |
| --- | --- | --- | --- | --- |
| | The Invention Hereunder | | Control Areas | |
| | Healthy | Semi-withered | Healthy | Semi-withered |
| Start | 46.00 cm | 46.15 cm | 44.42 cm | 45.35 cm |
| Finish | 48.74 cm | 48.85 cm | 46.50 cm | 47.06 cm |

| Comparison of the diameter of seedlings | | | | |
| --- | --- | --- | --- | --- |
| | The Invention Hereunder | | Control Areas | |
| | Healthy | Semi-withered | Healthy | Semi-withered |
| Start | 1.07 cm | 1.05 cm | 1.05 cm | 1.12 cm |
| Finish | 1.40 cm | 1.38 cm | 1.19 cm | 1.24 cm |

EXAMPLE 7

Experiment Regarding Preventing Damage Caused by Repeated Crops

Okra is cultivated on such soil (24 square meters) that has been damaged by repeated cropping.

| | |
| --- | --- |
| April 2 | Seeds planted in soil which has been covered and kept warm for one week |
| April 17 | Budding |
| April 13–18 | Seeds planted again replacing those budded but not growing |
| May 2–8 | Seedlings from the seeds planted on April 19th supplemented |
| May 10 | Seeds planted 4–5 times, but no more after that day |
| May 22 | Watering |
| May 27 | The cover is removed |
| May 29 | Stevia powder sprayed with sprinkled water over soil at the ratio of 5 g per square meter |
| June 6 | The work of May 29th repeated. The leaves of the okra fall off and the stalks start leaning |
| June 9 | Stevia powder sprayed with sprinkled water over the surface of the soil at the ratio of 7 g per square meter |
| June 18 | The work of June 9th repeated. The leaves of the okra are revitalized |
| June 22 | Stevia powder sprayed with sprinkled water over the surface of the soil at the ratio of 4 g per square meter |
| July 8 | The work of June 22$^{nd}$ is repeated. The okra completely recovers and becomes about identical to that growing on soil which has no damage caused by repeated crops |

The causes of damage by repeated crops are considered to be as follows:

(1) Substances that leak out of the root of a plant accumulate in the soil and cause damage directly to the plant;

(2) The accumulated substances are detrimental to the flora in the soil, such as useful bacteria like bactobaccilus, actimycetes, photosynthetic bacteria, and so forth, and accelerate adhesion of hazardous microbes;

(3) Depending upon the kind of plants, trace elements required by the plants become deficient.

The invention hereunder activates the useful microbes in the soil and proliferates them 100–1000 times so as to overcome damage caused by the repeated crops.

EXAMPLE 8

Experiment Regarding the Rooting of Fruit Trees

The experiment is conducted in the warm Southwestern area of Kyushu. 75 Dekopon trees onto which 1–2 year old seedlings of a trifoliate orange have been grafted are planted in a 1000 square meters orchard and grown for 3 years. Then, in a first harvest year, 1.1 tons of Dekopon are harvested. After the harvest, the surface of the soil is scraped and the conditions of the roots is investigated. As a result, it is found that the number of the fine roots, which growing points at their tips, has decreased tremendously. The second year's crop is reduced tremendously. The orchard is divided into four approximately equal experimental areas. Yields from each of the areas, which are, of course, approximately 250 square meters, are extrapolated to a 1000 square meters basis.

In all experimental areas, a commercially available mixed fertilizer containing, by weight, more than 70% organic materials, 8% nitrogen (N), 7% phosphorus (P), and 6% potassium (K) is applied four times (in March, May, September, and November) at the ratio of 4–5 bags (20 kg per bag) per 1000 square meters.

Treatment with Stevia powder is carried out in the experimental area 1 by spraying 2400 times diluted Stevia extract over the surface of the leaves of the trees, one month after the application of the Stevia powder, at the ratio of 600 liters per 1000 square meters, and repeating the same treatment three times every other week. The Stevia extract is made by boiling the leaves and the stalk of the Stevia plant in water down to a concentration of 16% by weight and allowing it to cool. 1.2 liters of the Stevia extract is produced from 1kg of the Stevia plant. Placing the extract at room temperature, the extract starts fermenting and emitting carbon dioxide. The fermenting process is vigorous at the initial stage and gradually gets lesser at a later stage. The extract that is fermented for one year is used as the original liquid which is subsequently diluted by the ratio stated above.

In the third year, the number of roots has recovered, and 1.8 tons of Dekopon per 1000 square meters are harvested in the experimental area 1. After the harvesting, it is found that the numbers of fine roots have conspicuously decreased and the numbers of fruit coming into bearing have also conspicuously decreased. In the fifth year, the Stevia powder is sprayed around the roots of the trees at the ratio of 500–700 g per 1000 square meters and that area is then fully watered. At the end of the year, 1.9 tons of Dekopon are harvested.

The trees bear fruit every other year. The orchard is ranked above the average in terms of harvest (1.5 tons per 1000 square meters per crop).

In the experimental area 2, the trees are made to bear fruit every year by repeating the same Stevia powder treatment as in the experimental area 1 every May for 3 years. The crop increases year by year and eventually 3.1 tons per 1000 square meters of Dekopon is harvested.

In the experimental area 3, the same Stevia powder treatment as in experimental area 2 is conducted from the third year and the 2400 times diluted liquid of the Stevia extract is sprayed over the surface of the leaves at the ratio of 600 liters per 1000 square meters in the fifth year, this being repeated three times every other week.

The experimental area 4 is a control area and no Stevia treatment is conducted. The same fertilizer as used in the experimental area 1 is applied.

On July 16, the surface of the soil is scraped and the condition of the roots is surveyed, the results being shown in Table 2 below. The crop at the end of the fifth year is converted into weight (tons) per 1000 square meters, and, as well as the conditions of the roots after harvest, is included in Table 2. End portions of the main roots are cut off, washed with slowly running water, and evaluated according to the following rating standards below, in descending order:

W: White and transparent rootlets are densely intertwined at the tip of the main root;

D: The rootlets are dense;

C: The rootlets are not sufficient to create a dense configuration, but when scraped off, are capable of developing into fruit-bearing Dekopon trees;

N: The rootlets, when scraped off are not capable of developing into fruit-bearing Dekopon trees.

As clearly shown in Table 2, Stevia powder acts to dramatically increase the crop of Dekopon. Additionally, it also acts to improve the budding, expansion, thickness, and color of the leaves and to decrease the ratio of deformed or mutated fruits. Even though citrus trees are noted for their poor rooting, the Stevia powder enhances the rooting of the trees of Dekopon and is able to improve the rooting of various plants even when applied in small doses.

TABLE 2

| Experimental Area | | Condition of the Roots in July | The Crop in the 5th Year (tons/1000 square meters) | Condition of the Roots after Harvesting |
|---|---|---|---|---|
| 1 | 1 year after the Stevia powder treatment | D | 1.9 | C |
| 2 | 3 years after the Stevia powder treatment | W | 3.1 | D |
| 3 | 3 years after the Stevia powder treatment, the Stevia liquid being concurrently used only in the 3rd year | W | 3.9 | D |
| 4 | No Stevia treatment | C | 1.65 | N |

What is claimed is:

1. A method of cultivating plants thereby to achieve as an effect at least one of enhancing root growth of plants, prolonging freshness and tastiness of edible agricultural products yielded by the plants, and decreasing the dropping of fruit before harvest time, comprising applying Stevia to soil in which the plants are cultivated and/or to the plants in a quantity per unit area not greater than about 20 grams per square meter of soil effective for at least one of said effects, the Stevia being in the form of particles of Stevia of at least 10 μm diameter or a liquid extract of Stevia, the Stevia consisting of stalk and leaves harvested prior to budding of the Stevia plant, wherein said stalk and said leaves are in a weight ratio of about 8 parts of said stalk to about 2 parts of said leaves.

2. The method according to claim 1, wherein the Stevia is in the form of particles.

3. The method according to claim 1, wherein the Stevia is in the form of a liquid extract.

4. The method according to claim 3, wherein the liquid extract has been fermented.

5. The method according to claim 2, wherein the diameter of the particles is less than 100 µm.

6. The method according to claim 5, wherein said diameter is less than 50 µm.

7. The method according to claim 2, wherein the quantity per unit area is about 1 to about 20 grams per square meter of soil.

8. The method according to claim 2, wherein the quantity per unit area is about 2 to about 15 grams per square meter of the soil.

9. The method according to claim 2, wherein said amount being applied is about 5 to about 10 grams per square meter of the soil.

10. The method according to claim 3, wherein the solids content of the extract is about 13 to 18% by weight.

11. The method of claim 4, wherein a relatively concentrated fermented liquid extract of Stevia of solids concentration of about 13 to 18% by weight is prepared and then diluted with water to form the fermented liquid extract of Stevia applied to the soil in which the plants are cultivated and/or to the plants.

12. The method of claim 11, wherein the ratio of the volume of the water with which the concentrated fermented liquid extract of Stevia is diluted to the volume of the concentrated fermented liquid extract of Stevia is about 300 to 3000.

13. The method according to claim 1, wherein the Stevia is admixed with an organic acid.

14. The method according to claim 13, wherein the organic acid is at least one of acetic acid, lactic acid, propionic acid, citric acid, tartaric acid, malic acid, valeric acid and maleic acid.

15. The method according to claim 1, wherein the Stevia is applied to soil in which citrus trees are cultivated and/or to the leaves of the citrus trees to enhance root growth and, consequently, repeated fruit yield of the citrus trees.

16. The method according to claim 1, wherein the citrus trees are dekopon trees.

17. The method according to claim 1, wherein the Stevia is applied to soil in which spinach, peach trees or mandarin orange trees are cultivated, the spinach, peaches or mandarin oranges are harvested and the spinach, peaches or mandarin oranges are not consumed for a period of time sufficient for them to have substantially lost freshness and tastiness had Stevia not been applied to the soil in which they were cultivated but while they still retain their freshness and tastiness due to the application of the Stevia to the soil in which they were cultivated.

18. The method according to claim 1, wherein the Stevia is applied to soil in which peach trees, pear trees or apple trees are cultivated to decrease the dropping of fruit from the trees before harvest time.

* * * * *